(12) United States Patent  
Cai et al.

(10) Patent No.: US 11,066,401 B2  
(45) Date of Patent: Jul. 20, 2021

(54) PYRIMIDINE COMPOUND, CHLORIDE SALT THEREOF, AND MANUFACTURING AND APPLICATION OF SAME

(71) Applicant: SHENZHEN HAIBIN PHARMACEUTICAL CO., LTD, Shenzhen (CN)

(72) Inventors: Weihui Cai, Shanghai (CN); Yuanwei Zhang, Shanghai (CN); Fang Jin, Shanghai (CN)

(73) Assignee: Shenzhen Haiban Pharmaceutical Co., Ltd.

( * ) Notice: Subject to any disclaimer, the term of this patent is extended or adjusted under 35 U.S.C. 154(b) by 198 days.

(21) Appl. No.: 16/310,994

(22) PCT Filed: Feb. 15, 2017

(86) PCT No.: PCT/CN2017/073654  
§ 371 (c)(1),  
(2) Date: Dec. 18, 2018

(87) PCT Pub. No.: WO2017/219688  
PCT Pub. Date: Dec. 28, 2017

(65) Prior Publication Data  
US 2020/0247797 A1    Aug. 6, 2020

(30) Foreign Application Priority Data

Jun. 21, 2016 (CN) .......................... 201610450682.5

(51) Int. Cl.  
*C07D 417/14* (2006.01)  
*A61P 35/00* (2006.01)

(52) U.S. Cl.  
CPC ............ *C07D 417/14* (2013.01); *A61P 35/00* (2018.01); *C07B 2200/13* (2013.01)

(58) Field of Classification Search  
CPC .... A61P 35/00; C07B 2200/13; C07D 417/14  
See application file for complete search history.

(56) References Cited

FOREIGN PATENT DOCUMENTS

| CN | 102203079 A | 9/2011 |
| CN | 102924446 A | 2/2013 |
| CN | 108059631 | * 5/2018 |

* cited by examiner

*Primary Examiner* — Erich A Leeser  
(74) *Attorney, Agent, or Firm* — Lewis Roca Rothgerber Christie LLP

(57) ABSTRACT

The present invention relates to a pyrimidine compound, a chloride salt thereof, and a manufacturing and application of same. The chloride salt of the pyrimidine compound is presented by formula (II). The chloride salt has higher solubility, good stability, higher bioavailability, and very low hygroscopicity, and has excellent inhibition against a PIM kinase.

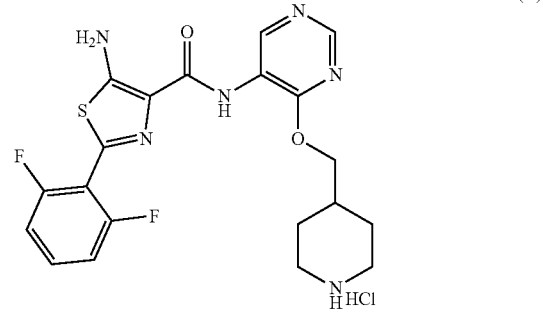

20 Claims, 3 Drawing Sheets

PYRIMIDINE COMPOUND, CHLORIDE SALT THEREOF, AND MANUFACTURING AND APPLICATION OF SAME

CROSS-REFERENCE TO RELATED APPLICATIONS

The present application is a National Phase Patent Application and claims priority to and the benefit of International Application Number PCT/CN2017/073654, filed on Feb. 15, 2017, which claims the priority and benefit of Chinese Patent Application No. 201610450682.5, filed on Jun. 21, 2016, the entire contents of all of which are incorporated herein by reference.

TECHNICAL FIELD

The present invention belongs to the technical field of organic synthesis and pharmaceutical application, specifically relates to a hydrochloride salt of pyrimidine compounds, preparation method and use thereof.

BACKGROUND ART

Research of anti-cancer drugs is a challenging and critical field in the current life science. Recently, along with further understanding on pathogenic mechanism of tumors, the basic process of changes of signal transduction pathway in tumor cells is progressively articulated. It has become one of effective ways to develop novel targeted anti-cancer drugs with strong efficiency, low toxicity and high specificity by utilizing crucial kinases in cell signaling pathway as drug screening targets. At present, it is estimated that more than ¼ of all the pharmacological targets are protein kinases, which is even up to 75% in anti-cancer field, wherein PIM (Provirus Integration site for Moloney leukemia) kinase is one of the hot research targets in recent years.

The PIM gene was first named as provirus integration site for Moloney leukemia virus. The PIM kinase is highly conserved through evolution of multicellular species, and it has three subtypes, they are PIM-1, PIM-2 and PIM-3 respectively, which all belong to serine/threonine protein kinases. The subtypes of PIM kinase are overexpressed in multiple human tumor cells, which affect the proliferation and survival of tumor cells through multiple mechanism: PIM kinase promotes tumor cell hyperplasia through synergistic reaction with transcription factors; PIM kinase also increases tumor cells survival through phosphorylation of apoptosis protein BAD and ASK1; PIM kinase regulates cell cycle and induces cellular hyperplasia through controlling multiple cell cycle factors; PIM kinase improves cell survival ability through controlling cell signaling pathways; PIM kinase modulates cellular hyperplasia and apoptosis by directly affecting Bcl-2 phosphorylation and other protein substrates such as MYC, Histone H3, p21, p27, CDC25A, CDC25C and CXR4, which plays an important role in cell cycle regulation and development and progression of tumors.

PIM kinase inhibitors have following characteristics:

(1) wide expression: PIM kinase may inhibit apoptosis which is closely related with the tumor development, over expression of PIM kinase has been found in various liquid and solid tumor, therefore, preclinical and clinical researches reported that PIM kinase inhibitors have remarkable effect on multiple tumors.

(2) low toxicity: Unlike common protein kinase targets, the inhibition of PIM kinase can lead to apoptosis of tumor cells without affecting other functions of animals. Therefore, anti-tumor drugs developed from PIM kinase inhibitors might exhibit much lower toxicity than existing kinase inhibitors.

(3) broad application: PIM kinase inhibitors can be used solely or in combination with other anti-tumor drugs to treat tumors.

The overexpression of PIM kinases in tumors work on the survival and diffusion of tumor cells, therefore, the inhibition on overexpression of PIM kinases in tumors is an effective therapeutic method. Besides for treating tumor, PIM kinase inhibitors also can be used to treat immunological diseases, allergy and immune response after organ transplant (Immunology, 116, 82-88, 2005).

CN201210271738.2 describes a kinase inhibitor, preparation method and use. The general formula comprises a large class of compounds, 63 compounds are prepared in the examples, it also discloses that all compounds of examples 1-63 significantly inhibit PIM kinases, among which more than 50 compounds are preferred; however, all these compounds are just listed in free form.

In pharmaceutical field, besides the activity, the solubility, stability, hygroscopicity and bio-availability of compounds as therapeutic agents during processing, manufacturing and storing, etc. are essential to the development of drugs, so it is great important to search for compounds and salts thereof, which are suitable for pharmaceutical use.

SUMMARY OF THE INVENTION

The purposes of the present invention are to provide a pharmaceutical salt of 5-amino-2-(2,6-difluorophenyl)-N-(4-(piperidine-4-methoxy)pyrimidine-5-) thiazole-4-formamide (as shown in Formula (I)) having high solubility, good stability, low hygroscopicity, high bioavailability and desirable activity to PIM kinase, its crystalline form and a pharmaceutical composition comprising the same as an active component and to provide a method for manufacturing the pharmaceutical salt and a use of the pharmaceutical salt and the pharmaceutical composition in preparing drugs for the treatment of diseases caused by overexpression of PIM kinase.

The technical solution of the present invention is described as below: In one aspect, the present invention provides a hydrochloride salt of a compound shown in Formula (I), wherein the structure of the hydrochloride salt is shown in Formula (II):

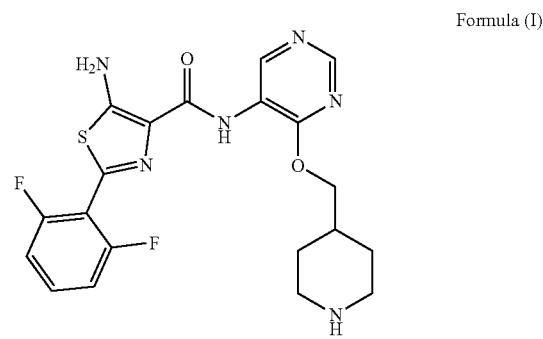 [SMILES: Nc1sc(-c2c(F)cccc2F)nc1C(=O)Nc1cncnc1OCC1CCNCC1 ; Cl]

Formula (I)

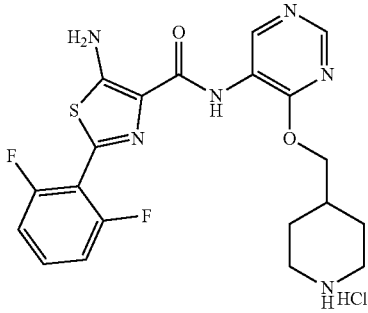

Formula (II)

wherein, the compound shown in Formula (I) is 5-amino-2-(2,6-difluorophenyl)-N-(4-(piperidine-4-methoxy)pyrimidine-5-) thiazole-4-formamide.

Preferably, the hydrochloride salt is present in a crystalline form.

Preferably, the X-ray powder diffraction pattern of the crystalline form of the hydrochloride salt includes the diffraction peaks at 2θ of 6.8±0.20, 9.5±0.2 11.4±0.2°, 15.0±0.2°, 17.0±0.2°, 19.9±0.2°, 20.3±0.2°, 20.6±0.2°, 22.9±0.2°, 23.6±0.2°, 24.9±0.2°, 26.1±0.2° and 26.6±0.2°.

Preferably, the X-ray powder diffraction pattern of the crystalline form of the hydrochloride salt further includes the diffraction peaks at 2θ of 12.0±0.2°, 28.8±0.2°, 29.1±0.2°, 32.5±0.2° and 34.7±0.2°.

Preferably, the X-ray powder diffraction pattern of the crystalline form of the hydrochloride salt is shown as FIG. 3.

The angles 2θ are obtained by selecting the main peaks having strong relative strong intensity from the X-ray powder diffraction pattern, and the structure of the crystalline form of the hydrochloride salt may not be defined only by these values, i.e. other peaks may be included except for the peaks listed above. In addition, when X-ray is utilized to detect a crystal, some errors can be caused by measuring apparatus, measuring conditions, and adhering solvent and so on. For example, the angles 2θ may contain measurement error about ±0.2°, therefore when identifying the structure of the crystal, some errors should be considered, and the crystalline form, which has the substantially same pattern as the above X-ray powder diffraction pattern, is within the scope of the present invention.

In another aspect, the present invention provides a method of preparing above-mentioned hydrochloride salt comprising dissolving the compound shown in Formula (I) in a solvent, controlling the reaction temperature, adding a methanol solution of hydrogen chloride, reacting for 0 to 24 h under maintaining the reaction temperature, precipitating a solid from the reaction solution, filtering and drying under vacuum.

Preferably, in above-mentioned method, the reaction temperature is controlled at 0~30° C., preferably 0° C. or 20~30° C.

Preferably, in above-mentioned method, after adding the methanol solution of hydrogen chloride, the reaction lasts for 30 minutes to 24 hours, preferably 30 minutes under maintaining the reaction temperature.

Preferably, in above-mentioned method, the temperature of the drying under vacuum is 50° C.

Preferably, the method comprises dissolving the compound shown in Formula (I) in a solvent, heating it to 50~200° C., preferably 50~100° C., adding a methanol solution of hydrogen chloride, reacting for 0~24 hours at temperature of 50~100° C., then cooling down to 20~30° C., precipitating a solid from the reaction solution, filtering and drying under vacuum.

Preferably, in above-mentioned method, the compound shown in Formula (I) is dissolved in a solvent and then heated to 50~60° C.

Preferably, in above-mentioned method, after adding the methanol solution of hydrogen chloride, the reaction lasts for 0~24 hours, preferably 5~10 hours, more preferably 5 hours at temperature of 50~60° C.

Preferably, in above-mentioned method, the temperature of the drying under vacuum is 50° C.

Preferably, in above-mentioned method, the solvent is one or more selected from the group consisting of methanol, dichloromethane, dimethyl sulfoxide (DMSO), tetrahydrofuran, dimethylformamide (DMF), acetone, ethanol, acetonitrile, propanol, butanol, N-methylpyrrolidone (NMP), ethyl acetate and water.

More preferably, the solvent is one or more selected from the group consisting of methanol, dichloromethane, dimethyl sulfoxide, tetrahydrofuran, dimethylformamide, acetone, ethanol, acetonitrile, N-methylpyrrolidone, ethyl acetate and water.

Further preferably, the solvent is methanol and dichloromethane, dimethyl sulfoxide and tetrahydrofuran, dimethylformamide and acetone, ethanol and acetonitrile, N-methylpyrrolidone and ethyl acetate, N-methylpyrrolidone and water, or N-methylpyrrolidone.

Most preferably, the solvent is DMF and acetone.

Preferably, in above-mentioned method, the concentration of the methanol solution of hydrogen chloride is 0.25 mol/L~2 mol/L, preferred 0.5 mol/L~1 mol/L.

Preferably, in above-mentioned method, the mole ratio of the methanol solution of hydrogen chloride to the compound shown in Formula (I) is 0.1~10:1, preferred 1~1.5:1.

Hydrogen chloride can be replaced by different inorganic acids or organic acids, and different acid addition salts of the compound shown in Formula (I) can be prepared by adopting the method similar to that described as above.

In still another aspect, the present invention provides a pharmaceutical composition, which comprises the above-mentioned hydrochloride salt as an active component.

Preferably, the pharmaceutical composition comprises a pharmaceutically acceptable carrier or excipient.

Preferably, the pharmaceutical composition is in the form of tablet, capsule, pill, granule, powder, suppository, injection, solution, suspension, ointment, patch, lotion, drops, liniment or spray.

In still another aspect, the present invention further provides a use of the above-mentioned hydrochloride salt or the pharmaceutical composition comprising the hydrochloride salt as an active component in preparing drugs for the treatment of diseases caused by overexpression of PIM kinase.

Preferably, said diseases include tumor, autoimmune diseases, allergic diseases, atherosclerosis disease and rejection resulting from organ transplants.

In addition, the present invention further provides a method for treating diseases caused by over-expression of PIM kinase comprising administering an effective dose of the above-mentioned hydrochloride salt of the compound shown in Formula (I) or the pharmaceutical composition comprising the hydrochloride salt of the compound shown in Formula (I) as an active component to a subject in need thereof.

Preferably, the subject is a mammal.

Preferably, the diseases include tumor, autoimmune diseases, allergic diseases, atherosclerosis disease and rejection resulting from organ transplants.

The applicant believes that those skilled in the art can replace hydrogen chloride with different inorganic acids or organic acids and prepare different acid addition salts of the compound shown in Formula (I) by adopting the method of the present invention or the method similar to that of the present invention, however, the hydrochloride salt of the present invention has significant technical advantages compared with other acid addition salts:
(1) the hydrochloride salt of the present invention has high solubility, the solubility in water is about 1 mg/mL, which benefits the preparation of formulation and in vivo absorption thereof.
(2) the hydrochloride salt of the present invention has low hygroscopicity, the weight increase by hygroscopy was only 0.52% in the hygroscopicity test according to Chinese Pharmacopoeia; the hydrochloride salt has high stability, i.e., the hydrochloride salt is stable against heat, light and high humidity, the stability test was performed according to Chinese Pharmacopoeia, the amount of related substance was determined after 10 days, the result shows that the amount of related substance of the hydrochloride salt of the present invention increased≤0.19%.
(3) the hydrochloride salt of the present invention has higher bioavailability in animals when compared with other salts.
(4) the hydrochloride salt of the present invention has very higher inhibitory activities to three kinds of PIM kinase, which is suitable for preparing drugs for the treatment of diseases caused by over-expression of PIM kinase, such as tumor, autoimmune diseases, allergy and immune reaction after organ transplants, etc.

BRIEF DESCRIPTION OF THE DRAWINGS

The following figures are used as supplementary explanation for the embodiments of the present invention, wherein.

EXAMPLES

Figure 1:
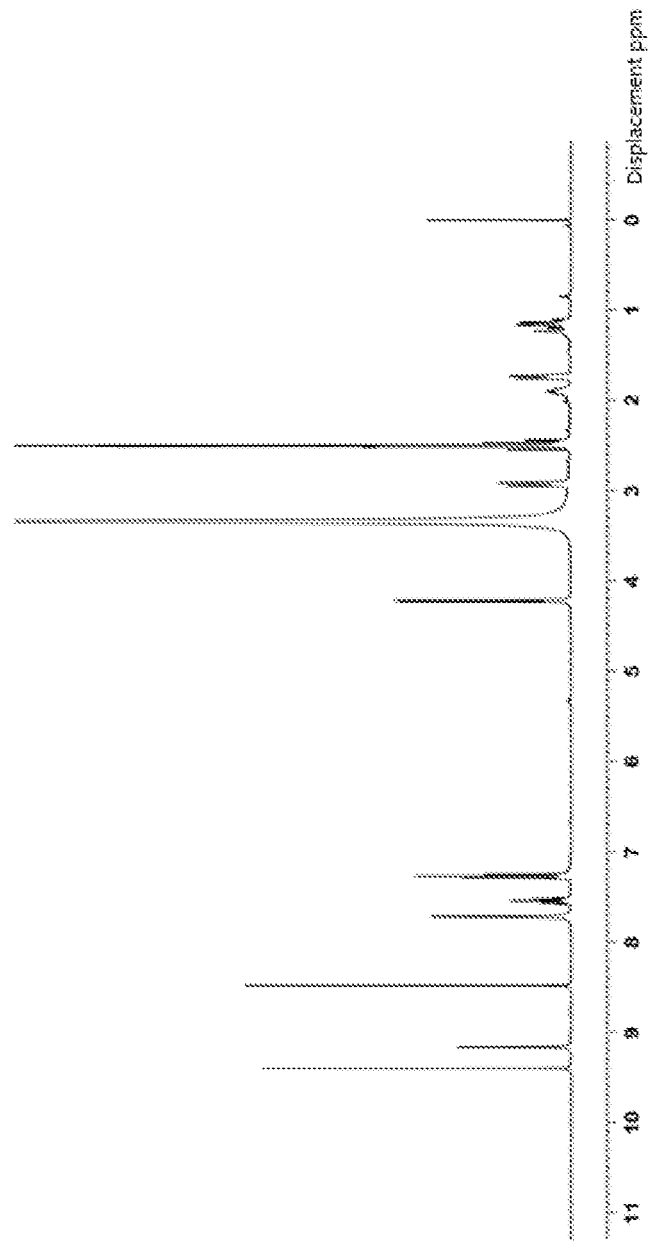
FIG. 1 shows the $^1$HNMR spectrum of the hydrochloride salt of the compound shown in formula (I) prepared in Example 2.

The present invention is further illustrated through combining the following specific examples. It should be understood that the examples of the present invention are only used for explaining the present invention, rather than limiting the scope of the present invention.

The experimental methods without specific conditions in the following examples are usually carried out according to the conventional conditions or the conditions of suggested by manufacturers. Unless otherwise defined, all professional and scientific terms in the description have the same meaning that is familiar to those skilled in the art.

In addition, any methods and materials similar or equivalent to those described herein can be used in the method of the present invention. The preferred implementation method and materials herein are only used for demonstration.

Example 1 Preparation of the Compound Shown in Formula (I)

1) Preparation of tert-butyl 4-((5-amino-pyrimidinyl-4-oxy) methyl) piperidine-1-carboxylate (SM-3)

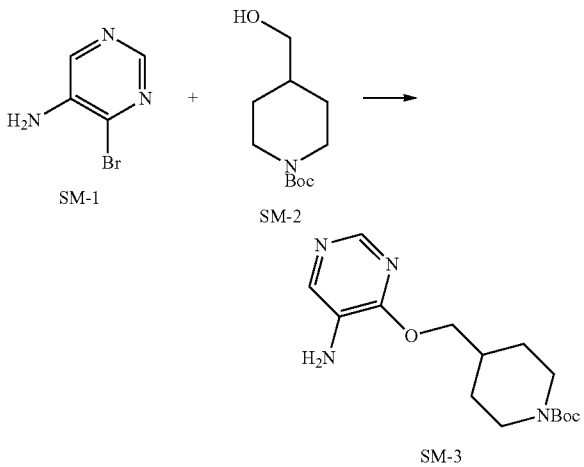

Under room temperature (25° C.), NaH (71 mg, 2.94 mmol) was added to 4-hydroxymethyl-piperidine-1-carboxylate (SM-2) (574 mg, 2.67 mmol) in THF (tetrahydrofuran) (10 mL) and stirred for 1 hour, and then 4-bromopyrimidine-5-amine (SM-1) (348 mg, 2.67 mmol) was added thereinto. The reactant was heated to 100° C. under nitrogen protection, stirred for 4 hours, and then concentrated in a vacuum rotatory evaporator at room temperature (20-30° C.). The residue after concentration was purified by silica gel chromatography (the used eluent was: 10-30% ethyl acetate/petrol) to give tert-butyl 4-((5-amino-pyrimidinyl-4-oxy) methyl) piperidine-1-carboxylate (SM-3) (370 mg, 1.2 mmol).

2) Preparation of tert-butyl 4-((5-(5-amino-2-(2,6-difluorophenyl) thiazole-4-carboxamide) pyrimidine-4-oxy) methyl) piperidine-1-carboxylate (SM-5)

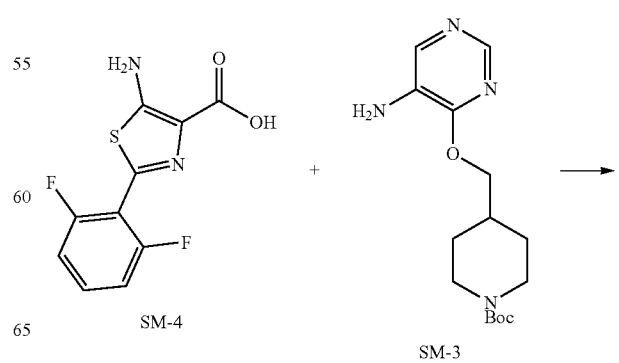

-continued

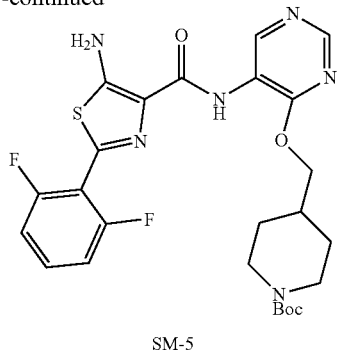

SM-5

A mixture of compound (SM-3) (52 mg, 0.169 mmol), compound 5-amino-2-(2,6-difluorophenyl) thiazole-4-carboxylic acid (1E) (SM-4) (40 mg, 0.169 mmol), HATU (77 mg, 0.203 mmol) and DIEA (93 μL, 0.507 mmol) in DMF (5 mL) was stirred for 1 hour at 50° C., diluted with ethyl acetate (50 mL) after cooling and then washed with saturated salt water. The organic phase was concentrated in a vacuum rotatory evaporator at room temperature (20-30° C.) after drying with $Na_2SO_4$. The residue after concentration was purified by silica gel chromatography (the used eluent was: 10-30% ethyl acetate/petrol) to give tert-butyl 4-((5-(5-amino-2-(2,6-difluorophenyl) thiazole-4-carboxamide) pyrimidine-4-oxy) methyl) piperidine-1-carboxylate (SM-5) (32 mg, 0.0585 mmol).

3) Preparation of 5-amino-2-(2,6-difluorophenyl)-N-(4-(piperidine-4-methoxy) pyrimidine-5-) thiazole-4-formamide (the compound shown in Formula (I))

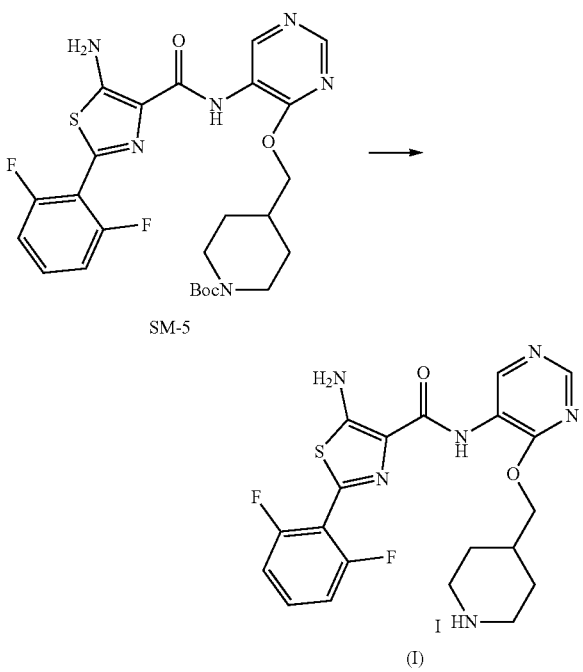

At room temperature (25° C.), TFA (trifluoracetic acid) (0.5 mL) was added to compound (SM-5) (21 mg, 0.0384 mmol) in $CH_2Cl_2$ (1 mL), stirred for 10 minutes, and then concentrated in a vacuum rotatory evaporator at room temperature (25° C.), the residue was dissolved in $CH_2Cl_2$ (10 mL), washed respectively with 1 equivalent NaOH (5 mL) and saturated salt water (5 mL), the organic phase was dried with $Na_2SO_4$, and then concentrated in a vacuum rotatory evaporator at room temperature (25° C.) to give the product of 5-amino-2-(2,6-difluorophenyl)-N-(4-(piperidine-4-methoxy) pyrimidine-5-) thiazole-4-formamide (the compound shown in formula (I)) (11 mg, 0.0246 mmol).

$^1$H NMR (400 MHz, CD3OD): δ ppm 1.26-1.29 (m, 2H), 1.91-1.94 (m, 2H), 2.04-2.12 (m, 1H), 2.66-2.69 (m, 2H), 3.10-3.13 (m, 2H), 3.90-3.98 (m, 2H), 6.99-7.02 (m, 2H), 7.31-7.41 (m, 1H), 8.33 (s, 1H), 9.40 (s, 1H).

MS (ESI) 447 m/z (M+H).

Example 2 Preparation of Hydrochloride Salt of the Compound Shown in Formula (I)

50 mg of the compound shown in formula (I) prepared in EXAMPLE 1(0.11 mmol), 2 ml methanol and 8 ml dichloromethane were added into a reaction bottle, stirred until the solution became clear at 20~30° C., 165 μl 1N methanol solution of hydrochloric acid (0.165 mmol) was added in one portion, the solution became muddy slowly, stirred for half an hour at 20~30° C., filtered, and then the filter cake was dried under vacuum at 50° C. to obtain 30 mg of almost white solid with a yield of 56.5%, mp: 236.1~239.4° C.

Figure 2:
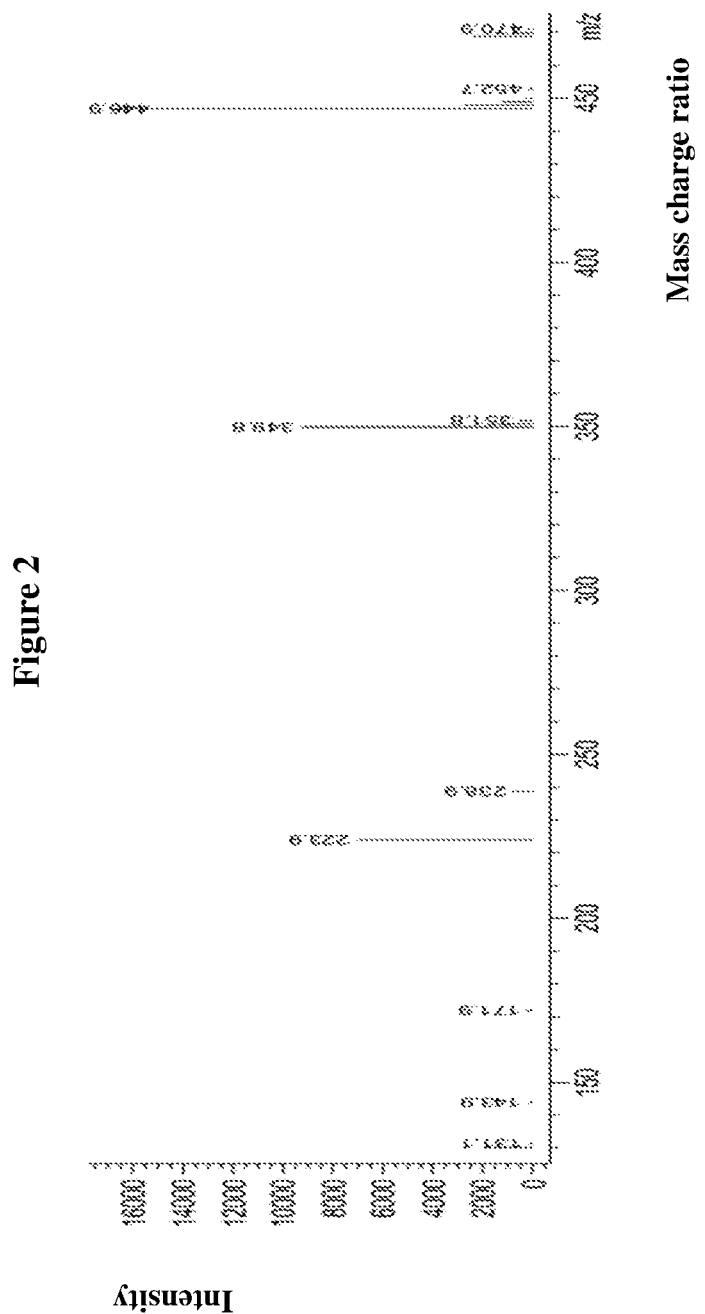
FIG. 2 shows the mass spectrum of the hydrochloride salt of the compound shown in formula (I) prepared in Example 2.

Wherein, the $^1$HNMR (400 MHz, DMSO-$d_6$) spectrum was shown as FIG. 1, the mass spectrum was shown as FIG. 2, wherein m/z: 446.9 [(M−HCl)+H]+.

Figure 3:
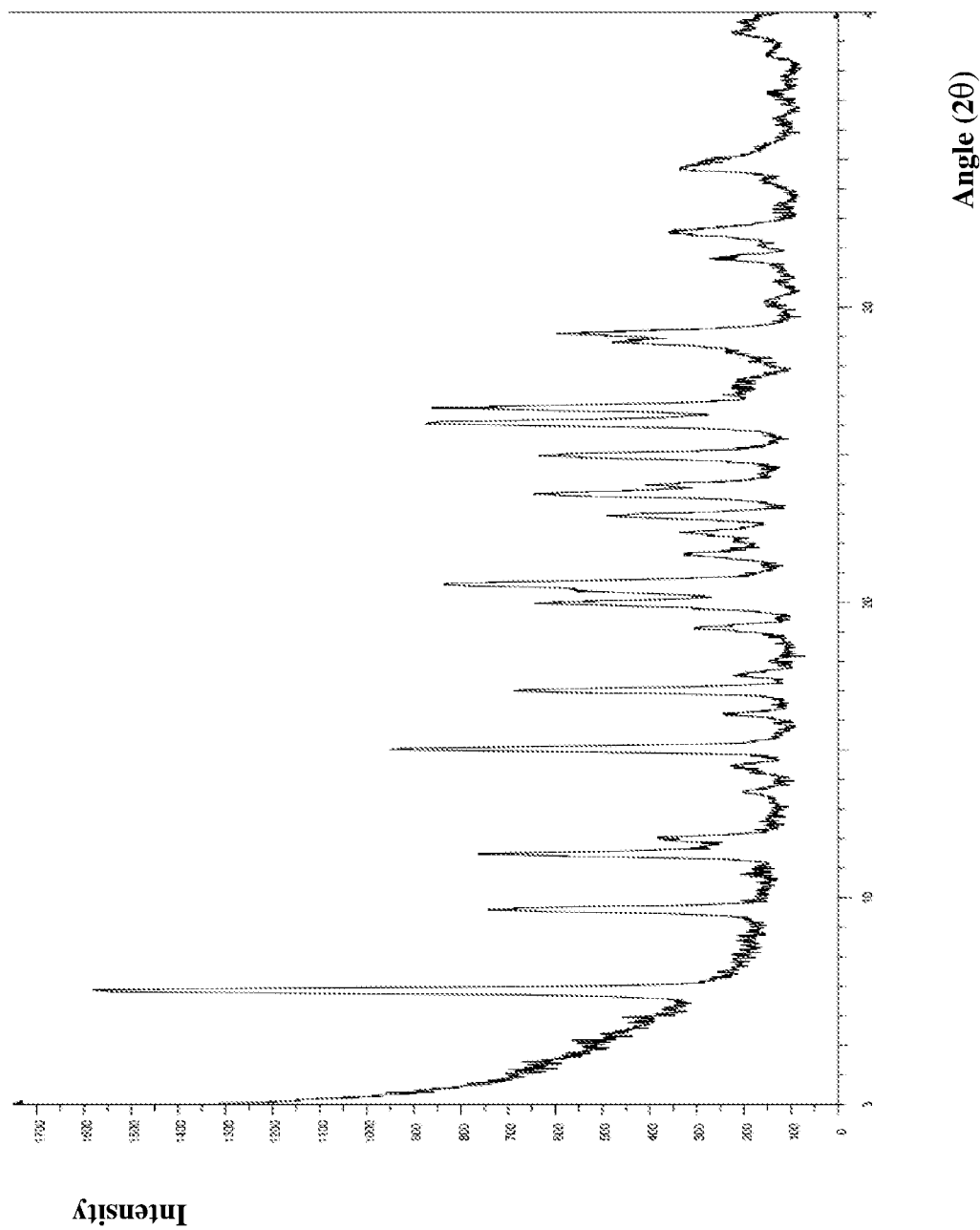
FIG. 3 shows the X-ray powder diffraction pattern of the hydrochloride salt of the compound shown in formula (I) prepared in Example 2.

The prepared hydrochloride salt of the compound shown in formula (I) is a crystal, the X-ray diffraction pattern of the crystal was shown as FIG. 3, the detecting condition is shown as below and the detecting results are listed in Table 1:

Detecting apparatus: Bruker D8Advance X-ray diffractometer

Detecting conditions: target material was Cu, 2θ scan started at 3.000, 2θ scan ended at 40.000, the voltage was 40 KV, the current was 40 mA, Ka1=1.54060, Ka2=1.54439, Ka2/Ka1=0.5, Ka=1.54186.

TABLE 1

X-ray Diffraction Pattern Datum of The Compound Shown in Formula (I)

| No. | Angle 2θ | Counts | Intensity (%) |
|---|---|---|---|
| 1 | 6.8 | 1590 | 100 |
| 2 | 9.5 | 747 | 47 |
| 3 | 11.4 | 760 | 47.8 |
| 4 | 12.0 | 391 | 24.6 |
| 5 | 15.0 | 957 | 60.2 |
| 6 | 17.0 | 692 | 43.5 |
| 7 | 19.9 | 659 | 41.4 |
| 8 | 20.3 | 547 | 34.4 |
| 9 | 20.6 | 846 | 53.2 |
| 10 | 22.9 | 491 | 30.9 |
| 11 | 23.6 | 642 | 40.4 |
| 12 | 24.9 | 635 | 39.9 |
| 13 | 26.1 | 870 | 54.7 |
| 14 | 26.6 | 861 | 54.2 |
| 15 | 28.8 | 475 | 29.9 |
| 16 | 29.1 | 597 | 37.5 |
| 17 | 32.5 | 365 | 23 |
| 18 | 34.7 | 345 | 21.7 |

Example 3 Preparation of Hydrobromide of the Compound Shown in Formula (I)

50 mg of the compound shown in formula (I) prepared in EXAMPLE 1(0.11 mmol), 2 ml methanol and 8 ml dichloromethane were added into a reaction bottle, stirred until the solution became clear at 20~30° C., a mixed solution of 30% of 44 mg hydrobromic acid (0.163 mmol) and 0.5 ml methanol was added in one portion, the solution became muddy slowly, stirred for half an hour at 20~30° C. and then filtered, the filter cake was dried under vacuum at 50° C. to obtain 24 mg of almost white solid with a yield of 41.3%, mp: 225.1-227.7° C., m/z: 446.9[(M−HBr)+H]+.

Example 4 Preparation of Maleate of the Compound Shown in Formula (I)

50 mg of the compound shown in formula (I) prepared in EXAMPLE 1(0.11 mmol), 2 ml methanol and 8 ml dichloromethane were added into a reaction bottle, stirred until the solution became clear at 20~30° C., a mixed solution of 19 mg maleic acid (0.164 mmol) and 0.5 ml methanol was added in one portion, the solution became muddy slowly, stirred for half an hour at 20~30° C., and then filtered, the filter cake was dried under vacuum at 50° C. to obtain 48 mg of almost white solid with a yield of 77.6%, mp: 235.1~240.7° C., m/z: 446.9[(M-$C_4H_4O_4$)+H]+.

Example 5 Preparation of Phosphate of the Compound Shown in Formula (I)

50 mg of the compound shown in formula (I) prepared in EXAMPLE 1(0.11 mmol), 2 ml methanol and 8 ml dichloromethane were added into a reaction bottle, stirred until the solution became clear at 20~30° C., a mixed solution of 5 mg phosphoric acid (0.051 mmol) and 0.5 ml methanol was added in one portion, the solution became muddy slowly, stirred for half an hour at 20~30° C., and then filtered, the filter cake was dried under vacuum at 50° C. to obtain 50 mg of almost white solid with a yield of 94.9%, mp: 222.3~224.8° C., m/z: 446.9[(M−$H_3PO_4$)+H]+.

Example 6 Preparation of Succinate of the Compound Shown in Formula (I)

50 mg of the compound shown in formula (I) prepared in EXAMPLE 1(0.11 mmol), 2 ml methanol and 8 ml dichloromethane were added into a reaction bottle, stirred until the solution became clear at 20~30° C., a mixed solution of 19 mg succinic acid (0.161 mmol) and 0.5 ml methanol was added in one portion, the solution became muddy slowly, stirred for half an hour at 20~30° C., and then filtered, the filter cake was dried under vacuum at 50° C. to obtain 46 mg of almost white solid with a yield of 74%, mp: 229.2~233.5° C., m/z: 446.9[(M-$C_4H_6O_4$)+H]+.

Example 7 Preparation of Sulphate of the Compound Shown in Formula (I)

50 mg of the compound shown in formula (I) prepared in EXAMPLE 1(0.11 mmol), 2 ml methanol and 8 ml dichloromethane were added into a reaction bottle, stirred until the solution became clear at 20~30° C., a mixed solution of 8 mg sulphuric acid (0.081 mmol) and 0.5 ml methanol was added in one portion, the solution became muddy slowly, stirred for half an hour at 20~30° C., and then filtered, the filter cake was dried under vacuum at 50° C. to obtain 53 mg of almost white solid with a yield of 88.5%, mp: 231.5~236.9° C., m/z: 446.9[(M−$H_2SO_4$)+H]+.

Example 8 Preparation of Citrate of the Compound Shown in Formula (I)

50 mg of the compound shown in formula (I) prepared in EXAMPLE 1(0.11 mmol), 2 ml methanol and 8 ml dichloromethane were added into a reaction bottle, stirred until the solution became clear at 20~30° C., a mixed solution of 32 mg citric acid (0.167 mmol) and 15 ml methanol was added in one portion, the solution became muddy slowly, stirred for half an hour at 20~30° C., and then filtered, the filter cake was dried under vacuum at 50° C. to obtain 54 mg of almost white solid with a yield of 76.9%, mp: 245.3~249.5° C., m/z: 446.9[(M-$C_6H_8O_7$)+H]+.

Example 9 Preparation of Benzoate of the Compound Shown in Formula (I)

50 mg of the compound shown in formula (I) prepared in EXAMPLE 1(0.11 mmol), 2 ml methanol and 8 ml dichloromethane were added into a reaction bottle, stirred until the solution became clear at 20~30° C., a mixed solution of 20 mg benzoic acid (0.164 mmol) and 0.5 ml methanol was added in one portion, the solution was clear, stirred for half an hour at 20~30° C., the solvent was evaporated under reduced pressure at 50° C., 10 ml dichloromethane was added and stirred for half an hour at 20~30° C., and then filtered, the filter cake was dried under vacuum at 50° C. to obtain 48 mg of almost white solid with a yield of 76.7%, mp: 247.3~252.7° C., m/z: 446.9[(M-$C_7H_6O_2$)+H]+.

Example 10 Preparation of Mesylate of the Compound Shown in Formula (I)

50 mg of the compound shown in formula (I) prepared in EXAMPLE 1(0.11 mmol), 2 ml methanol and 8 ml dichloromethane were added into a reaction bottle, stirred until the solution became clear at 20~30° C., a mixed solution of 16 mg methanesulfonic acid (0.166 mmol) and 0.5 ml methanol was added in one portion, the solution was clear, stirred for half an hour at 20~30° C., the solvent was evaporated under reduced pressure at 50° C., 10 ml dichloromethane was added and stirred for half an hour at 20~30° C., and then filtered, the filter cake was dried under vacuum at 50° C. to obtain 37 mg of almost white solid with a yield of 62%, mp: 242.1-246.7° C., m/z: 446.9[(M-$CH_4O_3S$)+H]+.

Example 11 Preparation of Lactate of the Compound Shown in Formula (I)

50 mg of the compound shown in formula (I) prepared in EXAMPLE 1(0.11 mmol), 2 ml methanol and 8 ml dichloromethane were added into a reaction bottle, stirred until the solution became clear at 20~30° C., a mixed solution of 15 mg lactic acid (0.167 mmol) and 0.5 ml methanol was added in one portion, the solution was clear, stirred for half an hour at 20~30° C., the solvent was evaporated under reduced pressure at 50° C., 10 ml dichloromethane was added and stirred for half an hour at 20~30° C., and then filtered, the filter cake was dried under vacuum at 50° C. to obtain 36 mg of almost white solid with a yield of 61%, mp: 210.1~213.6° C., m/z: 446.9[(M-$C_3H_6O_3$)+H]+.

Example 12 Preparation of Acetate of the Compound Shown in Formula (I)

50 mg of the compound shown in formula (I) prepared in EXAMPLE 1(0.11 mmol), 2 ml methanol and 8 ml dichloromethane were added into a reaction bottle, stirred until the solution became clear at 20~30° C., a mixed solution of 10 mg acetic acid (0.167 mmol) and 0.5 ml methanol was added in one portion, the solution was clear, stirred for half an hour at 20~30° C., the solvent was evaporated under reduced pressure at 50° C., 10 ml dichloromethane was added and stirred for half an hour at 20~30° C., and then filtered, the filter cake was dried under vacuum at 50° C. to obtain 31 mg of almost white solid with a yield of 55.6%, mp: 232.2~233.7° C., m/z: 446.9[(M-CH$_3$COOH)+H]+.

Example 13 Preparation of Tosylate of the Compound Shown in Formula (I)

50 mg of the compound shown in formula (I) prepared in EXAMPLE 1(0.11 mmol), 2 ml methanol and 8 ml dichloromethane were added into a reaction bottle, stirred until the solution became clear at 20~30° C., a mixed solution of 28 mg p-toluene sulfonic acid (0.163 mmol) and 0.5 ml methanol was added in one portion, the solution was clear, stirred for half an hour at 20~30° C., the solvent was evaporated under reduced pressure at 50° C., 10 ml dichloromethane was added and stirred for half an hour at 20~30° C., and then filtered, the filter cake was dried under vacuum at 50° C. to obtain 36 mg of almost white solid with a yield of 76.7%, mp: 239.3-237.6° C., m/z: 446.9[(M-C$_7$H$_8$O$_3$S)+H]+.

Example 14 Preparation of Palmitate of the Compound Shown in Formula (I)

50 mg of the compound shown in formula (I) prepared in EXAMPLE 1(0.11 mmol), 2 ml methanol and 8 ml dichloromethane were added into a reaction bottle, stirred until the solution became clear at 20~30° C., a mixed solution of 42 mg palmitic acid (0.164 mmol) and 0.5 ml methanol was added in one portion, the solution was clear, stirred for half an hour at 20~30° C., the solvent was evaporated under reduced pressure at 50° C., 1 ml dichloromethane and 10 ml n-hexane were added and stirred for half an hour at 20~30° C., and then filtered, the filter cake was dried under vacuum at 50° C. to obtain 69 mg of almost white solid with a yield of 89.2%, mp: 245.1-247.7° C., m/z: 446.9[(M-C$_{16}$H$_{32}$O$_2$)+H]+.

Example 15 Preparation Fumarate of the Compound Shown in Formula (I)

50 mg of the compound shown in formula (I) prepared in EXAMPLE 1(0.11 mmol), 2 ml methanol and 8 ml dichloromethane were added into a reaction bottle, stirred until the solution became clear at 20~30° C., a mixed solution of 19 mg fumaric acid (0.164 mmol) and 0.5 ml methanol was added in one portion, the solution became muddy slowly, stirred for half an hour at 20~30° C., and then filtered, the filter cake was dried under vacuum at 50° C. to obtain 48 mg of almost white solid with a yield of 77.6%, mp: 236.8-240.7° C., m/z: 446.9[(M-C$_4$H$_4$O$_4$)+H]+.

Example 16 Preparation of L-Tartrate of the Compound Shown in Formula (I)

50 mg of the compound shown in formula (I) prepared in EXAMPLE 1(0.11 mmol), 2 ml methanol and 8 ml dichloromethane were added into a reaction bottle, stirred until the solution became clear at 20~30° C., a mixed solution of 25 mg L-tartaric acid (0.167 mmol) and 0.5 ml methanol was added in one portion, the solution became muddy slowly, stirred for half an hour at 20~30° C., and then filtered, the filter cake was dried under vacuum at 50° C. to obtain 52 mg of almost white solid with a yield of 79.2%, mp: 245.1~246.1° C., m/z: 446.9[(M-C$_4$H$_6$O$_6$)+H]+.

Example 17 Preparation of Ascorbate of Compound Shown in Formula (I)

50 mg of the compound shown in formula (I) prepared in EXAMPLE 1(0.11 mmol), 2 ml methanol and 8 ml dichloromethane were added into a reaction bottle, stirred until the solution became clear at 20~30° C., a mixed solution of 29 mg ascorbic acid (0.165 mmol) and 0.5 ml methanol was added in one portion, the solution was clear, stirred for half an hour at 20~30° C., the solvent was evaporated under reduced pressure at 50° C., 10 ml dichloromethane and 10 ml n-hexane were added and stirred for half an hour at 20~30° C., and then filtered, the filter cake was dried under vacuum at 50° C. to obtain 58 mg of almost white solid with a yield of 84.7%, mp: 252.2~254.9° C., m/z: 446.9[(M-C$_6$H$_8$O$_6$)+H]+.

Example 18 Preparation of Chloride Salt of Compound Shown in Formula (I)

50 mg of the compound shown in formula (I) prepared in EXAMPLE 1(0.11 mmol), 2 ml DMSO and 8 ml tetrahydrofuran were added into a reaction bottle, stirred until the solution became clear at 20~30° C., 230 μl 0.5N methanol solution of hydrochloric acid (0.165 mmol) was added in one portion, the solution became muddy slowly, stirred for half an hour at 20~30° C., and then filtered, the filter cake was dried under vacuum at 50° C. to obtain 25 mg of almost white solid with a yield of 46.2%, mp: 236.1~239.4° C., m/z: 446.9[(M−HCl)+H]+.

Wherein, the prepared hydrochloride salt of the compound shown in formula (I) is a crystal, the mass spectrum, $^1$HNMR (400 MHz, DMSO-d$_6$) spectrum and X-ray diffraction pattern of the crystal is similar to that in EXAMPLE 2.

Example 19 Preparation of Hydrochloride Salt of the Compound Shown in Formula (I)

50 mg of the compound shown in formula (I) prepared in EXAMPLE 1(0.11 mmol), 2 ml DMF and 8 ml acetone were added into a reaction bottle, stirred until the solution became clear at 20~30° C., 230 μl 0.5N methanol solution of hydrochloric acid (0.165 mmol) was added in one portion, the solution became muddy slowly, stirred for half an hour at 20~30° C., and then filtered, the filter cake was dried under vacuum at 50° C. to obtain 35 mg of almost white solid with a yield of 64.7%, mp: 236.1-239.4° C., m/z: 446.9[(M−HCl)+H]+.

Wherein, the prepared hydrochloride salt of the compound shown in formula (I) is a crystal, the mass spectrum, $^1$HNMR (400 MHz, DMSO-d$_6$) spectrum and X-ray diffraction of the crystal is similar to that in EXAMPLE 2.

Example 20 Preparation of Hydrochloride Salt of the Compound Shown in Formula (I)

50 mg of the compound shown in formula (I) prepared in EXAMPLE 1(0.11 mmol), 2 ml ethanol and 8 ml acetonitrile were added into a reaction bottle, heated to 50~60° C., 230 μl 0.5N methanol solution of hydrochloric acid (0.165 mmol) was added in one portion, the solution became muddy slowly, stirred for 5 hours at 50~60° C., and then stirred for half an hour at 20~30° C., filtered, the filter cake was dried under vacuum at 50° C. to obtain 20 mg of almost white solid with a yield of 37%, mp: 236.1~239.4° C., m/z: 446.9[(M−HCl)+H]+. Wherein, the prepared hydrochloride salt of the compound shown in formula (I) is a crystal, the mass spectrum, $^1$HNMR (400 MHz, DMSO-d$_6$) spectrum and X-ray diffraction of the crystal is similar to that in EXAMPLE 2.

Example 21 Preparation of Hydrochloride Salt of the Compound Shown in Formula (I)

50 mg of the compound shown in formula (I) prepared in EXAMPLE 1(0.11 mmol), 2 ml propanol and 4 ml butanol were added into a reaction bottle, heated to 70~80° C., 44 μl 0.25N methanol solution of hydrochloric acid (0.011 mmol) was added in one portion, the solution became muddy slowly, stirred for 10 hours at 70~80° C., and then stirred for half an hour at 20~30° C., filtered, the filter cake was dried under vacuum at 50° C. to obtain 3 mg of almost white solid with a yield of 5.5%, mp: 236.1-239.4° C., m/z: 446.9[(M−HCl)+H]+. Wherein, the prepared hydrochloride salt of the compound shown in formula (I) is a crystal, the mass spectrum, $^1$HNMR (400 MHz, DMSO-d$_6$) spectrum and X-ray diffraction is similar to that in EXAMPLE 2.

Example 22 Preparation of Hydrochloride Salt of the Compound Shown in Formula (I)

50 mg of the compound shown in formula (I) prepared in EXAMPLE 1(0.11 mmol), 2 ml NMP and 4 ml ethyl acetate were added into a reaction bottle, stirred until the solution became clear at 20~30° C., 550 μl 2N methanol solution of hydrochloric acid (1.1 mmol) was added in one portion, the solution became muddy slowly, stirred for 24 hours at 20~30° C., and then filtered, the filter cake was dried under vacuum at 50° C. to obtain 27 mg of almost white solid with a yield of 49.9%, mp: 236.1~239.4° C., m/z: 446.9[(M−HCl)+H]+.

Wherein, the prepared hydrochloride salt of the compound shown in formula (I) is a crystal, the mass spectrum, $^1$HNMR (400 MHz, DMSO-d$_6$) spectrum and X-ray diffraction is similar to that in EXAMPLE 2.

Example 23 Preparation of Hydrochloride Salt of the Compound Shown in Formula (I)

50 mg of the compound shown in formula (I) prepared in EXAMPLE 1(0.11 mmol), 8 ml NMP and 1 ml water were added into a reaction bottle, stirred until the solution became clear 20~30° C., 367 μl 1.5N methanol solution of hydrochloric acid (0.55 mmol) was added in one portion, the solution became muddy slowly, stirred for 24 hours at 20~30° C., and then filtered, the filter cake was dried under vacuum at 50° C. to obtain 17 mg of almost white solid with a yield of 31.4%, mp: 236.1~239.4° C., m/z: 446.9[(M−HCl)+H]+.

Wherein, the prepared hydrochloride salt of the compound shown in formula (I) is a crystal, the mass spectrum, $^1$HNMR (400 MHz, DMSO-d$_6$) spectrum and X-ray diffraction is similar to that in EXAMPLE 2.

Example 24 Preparation of Hydrochloride Salt of the Compound Shown in Formula (I)

50 mg of the compound shown in formula (I) prepared in EXAMPLE 1(0.11 mmol) and 8 ml NMP were added into a reaction bottle, stirred, heated to 200° C., 367 μl 1.5N methanol solution of hydrochloric acid (0.55 mmol) was added in one portion, stirred for 2 hours at 90~100° C., and then stirred for 1 hour at 20~30° C., and filtered, the filter cake was dried under vacuum at 50° C. to obtain 11 mg of almost white solid with a yield of 20.3%, mp: 236.1~239.4° C., m/z: 446.9[(M−HCl)+H]+.

Wherein, the prepared hydrochloride salt of the compound shown in formula (I) is a crystal, the mass spectrum, $^1$HNMR (400 MHz, DMSO-d$_6$) spectrum and X-ray diffraction is similar to that in EXAMPLE 2.

Example 25 Preparation of Hydrochloride Salt of the Compound Shown in Formula (I)

50 mg of the compound shown in formula (I) prepared in EXAMPLE 1(0.11 mmol) and 20 ml NMP were added into a reaction bottle, stirred, the temperature was decreased to 0° C. in an ice bath, 110 μl 1N methanol solution of hydrochloric acid (0.11 mmol) was added in one portion, stirred for 2 hours at 0° C., and then filtered, the filter cake was dried under vacuum at 50° C. to obtain 15 mg of almost white solid with a yield of 27.7%, mp: 236.1~239.4° C., m/z: 446.9[(M−HCl)+H]+. Wherein, the prepared hydrochloride salt of the compound shown in formula (I) is a crystal, the mass spectrum, $^1$HNMR (400 MHz, DMSO-d$_6$) spectrum and X-ray diffraction is similar to that in EXAMPLE 2.

Example 26 Preparation of Hydrochloride Salt of the Compound Shown in Formula (I)

50 mg of the compound shown in formula (I) prepared in EXAMPLE 1(0.11 mmol), 2 ml DMF and 8 ml acetone were added into a reaction bottle, stirred until the solution became clear at 20~30° C., 55 μl 1N methanol solution of hydrochloric acid (0.055 mmol) was added in one portion, the solution became muddy slowly, stirred for half an hour at 20~30° C., and filtered, the filter cake was dried under vacuum at 50° C. to obtain 12 mg of almost white solid with a yield of 22.2%, mp: 236.1-239.4° C., m/z: 446.9[(M−HCl)+H]+.

Wherein, the prepared hydrochloride salt of the compound shown in formula (I) is a crystal, the mass spectrum, $^1$HNMR (400 MHz, DMSO-d$_6$) spectrum and X-ray diffraction is similar to that in EXAMPLE 2.

Example 27 Preparation of Hydrochloride Salt of the Compound Shown in Formula (I)

50 mg of the compound shown in formula (I) prepared in EXAMPLE 1(0.11 mmol), 2 ml DMF and 8 ml acetone were added into a reaction bottle, heated to 50-60° C., 110 μl 1N methanol solution of hydrochloric acid (0.11 mmol) was added in one portion, the solution became muddy slowly, stirred for 5 hours at 50~60° C., then stirred for half an hour at 20~30° C., and then filtered, the filter cake was dried under vacuum at 50° C. to obtain 37 mg of almost white solid with a yield of 68.4%, mp: 236.1-239.4° C., m/z: 446.9[(M−HCl)+H]+.

Wherein, the prepared hydrochloride salt of the compound shown in formula (I) is a crystal, the mass spectrum, $^1$HNMR (400 MHz, DMSO-d$_6$) spectrum and X-ray diffraction is similar to that in EXAMPLE 2.

Example 28 Preparation of Hydrochloride Salt of the Compound Shown in Formula (I)

50 mg of the compound shown in formula (I) prepared in EXAMPLE 1(0.11 mmol), 2 ml DMF and 8 ml acetone were added into a reaction bottle, and stirred, the temperature was decreased to 0° C. in an ice bath, 230 μl 0.5N methanol solution of hydrochloric acid (0.165 mmol) was added in one portion, stirred for 2 hours at 0° C., and then filtered, the filter cake was dried under vacuum at 50° C. to obtain 21 mg of almost white solid with a yield of 38.9%, mp: 236.1~239.4° C., m/z: 446.9[(M−HCl)+H]+.

Wherein, the prepared hydrochloride salt of the compound shown in formula (I) is a crystal, the mass spectrum, $^1$HNMR (400 MHz, DMSO-$d_6$) spectrum and X-ray diffraction is similar to that in EXAMPLE 2.

Experimental Example 1 Test of Solubility

An appropriate amount of the compound and salts prepared in EXAMPLES 1-17 was weighed and suspended in 3 ml water, the suspension in duplicate was placed in constant temperature oscillator and oscillated at 37° C. for 24 hours, sampled, filtered through 0.22 μm hydrophilic membrane, the concentration of drugs was detected by HPLC, then the solubility was calculated.

Wherein, the chromatographic condition was shown as follows:

HPLC: Waters 2695 UV Detector

Chromatographic Column: C18

Column temperature: 25° C.

Detection wavelength: 322 nm

Sample volume: 10 μl

Mobile phase A: 0.1% TFA-water

Mobile phase B: 0.1% TFA-CAN

The gradient elution procedure was shown in Table 2, the solubility of the compound and salts prepared in EXAMPLES 1-17 was shown in Table 3:

TABLE 2

| Gradient Elution Procedure | | |
|---|---|---|
| Time(min) | Mobile phase A(%) | Mobile phase B(%) |
| 0 | 95 | 5 |
| 8 | 5 | 95 |
| 10 | 95 | 5 |
| 15 | 95 | 5 |

TABLE 3

Experimental Results of the Solubility of the Compound Shown in Formula (I) and Salts Thereof

| Example No. | Name | Solubility(μg/ml) |
|---|---|---|
| EXAMPLE 1 | Compound shown in formula (I) | 1.01 |
| EXAMPLE 2 | Hydrochloride salt | 995.29 |
| EXAMPLE 3 | Hydrobromide | 137.60 |
| EXAMPLE 4 | Maleate | 284.16 |
| EXAMPLE 5 | Phosphate | 247.72 |
| EXAMPLE 6 | Succinate | 19.08 |
| EXAMPLE 7 | Sulphate | 0.58 |
| EXAMPLE 8 | Citrate | 3.79 |
| EXAMPLE 9 | Benzoate | 28.75 |
| EXAMPLE 10 | Mesylate | 748.07 |
| EXAMPLE 11 | Lactate | 491.91 |
| EXAMPLE 12 | Acetate | 703.88 |
| EXAMPLE 13 | Tosylate | 0.61 |
| EXAMPLE 14 | Palmitate | 10.34 |
| EXAMPLE 15 | Fumarate | 0.08 |
| EXAMPLE 16 | Tartrate | 0.29 |
| EXAMPLE 17 | Ascorbate | 36.59 |

The results show that the solubility of hydrochloride salt of compound shown in Formula (I) was significantly higher than that of other salts.

Experimental Example 2 Test for Hygroscopicity

The experiment was carried out according to *Guiding Principles of Drug Hygroscopicity Test*, Appendix XIX J, Second Part, *Chinese Pharmacopeia* (2010), the weight increased by hygroscopy of samples (compound shown in Formula (I) and salts thereof prepared in EXAMPLES 1-17) was calculated respectively, the results were shown in Table 4.

TABLE 4

Experimental Results of Hygroscopicity of Compound Shown in Formula (I) and Salts Thereof

| Example No. | Name | Weight increased by hygroscopy (%) |
|---|---|---|
| EXAMPLE 1 | Compound shown in formula (I) | 3.35 |
| EXAMPLE 2 | Hydrochloride salt | 0.52 |
| EXAMPLE 3 | Hydrobromide | 4.32 |
| EXAMPLE 4 | Maleate | 5.45 |
| EXAMPLE 5 | Phosphate | 3.32 |
| EXAMPLE 6 | Succinate | 7.56 |
| EXAMPLE 7 | Sulphate | 3.56 |
| EXAMPLE 8 | Citrate | 5.67 |
| EXAMPLE 9 | Benzoate | 7.53 |
| EXAMPLE 10 | Mesylate | 8.21 |
| EXAMPLE 11 | Lactate | 3.67 |
| EXAMPLE 12 | Acetate | 9.21 |
| EXAMPLE 13 | Tosylate | 5.78 |
| EXAMPLE 14 | Palmitate | 6.43 |
| EXAMPLE 15 | Fumarate | 4.77 |
| EXAMPLE 16 | Tartrate | 7.88 |
| EXAMPLE 17 | Ascorbate | 5.67 |

The results show that the hygroscopicity of the hydrochloride salt of compound shown in Formula (I) was significantly lower than that of other salts.

Experimental Example 3 Test for Stability

The experiment was carried out according to *Guiding Principles of Active Pharmaceutical Ingredient and Pharmaceutical Formulation Stability Test*, Appendix XIX C, Second Part, *Chinese Pharmacopeia* (2010), the increase of related substance of the solution of compounds shown in formula (I) and salts thereof (EXAMPLES 1-17) under high temperature condition (60° C.) and illumination (the light intensity was 4500 lx±500 lx) was detected to evaluate the stability.

Wherein, the method for detecting related substance was shown as following:

HPLC: Waters 2695 UV Detector

Chromatographic Column: Diamonsil C18 (2) 5 μm, 150×4.6 mm

Detection wavelength: 322 nm

Column temperature: 30° C.

Sample volume: 10 μl

Mobile phase A: methanol

Mobile phase B: buffer (900 ml water+10 ml triethylamine+5 ml phosphoric acid, being diluted to 1000 ml with water)

The gradient elution procedure was shown in Table 5:

TABLE 5

Gradient Elution Procedure

| Time(min) | Mobile phase A(%) | Mobile phase B(%) | Flow rate(ml/min) |
|---|---|---|---|
| 0 | 20 | 80 | 1 |
| 40 | 80 | 20 | 1 |
| 50 | 20 | 80 | 1 |
| 65 | 20 | 80 | 1 |

The testing samples were prepared by using acetonitrile-water (1:1) solution with a concentration of 10-100 μg/ml, kept under high temperature (60° C.) and illumination (the light intensity was 4500 lx±500 lx) respectively for 10 days, the mass of related substance was determined on day 0 and day 10 (calculated by using area normalization), the results were shown in Table 6.

TABLE 6

Experimental Results of Stability

| Example No. | Name | Day 0 | Day 10 under high temperature | Day 10 under illumination condition |
|---|---|---|---|---|
| EXAMPLE 1 | Compound shown in formula (I) | 0.45 | 5.02 | 3.02 |
| EXAMPLE 2 | Hydrochloride salt | 0.49 | 0.68 | 0.56 |
| EXAMPLE 3 | Hydrobromide | 0.52 | 3.45 | 1.67 |
| EXAMPLE 4 | Maleate | 0.46 | 4.54 | 2.22 |
| EXAMPLE 5 | Phosphate | 0.65 | 3.53 | 1.79 |
| EXAMPLE 6 | Succinate | 0.55 | 8.82 | 4.56 |
| EXAMPLE 7 | Sulphate | 0.52 | 4.67 | 2.45 |
| EXAMPLE 8 | Citrate | 0.52 | 7.34 | 5.52 |
| EXAMPLE 9 | Benzoate | 0.56 | 5.56 | 4.44 |
| EXAMPLE 10 | Mesylate | 0.54 | 35.6 | 23.0 |
| EXAMPLE 11 | Lactate | 0.54 | 10.78 | 5.67 |
| EXAMPLE 12 | Acetate | 0.62 | 3.56 | 2.65 |
| EXAMPLE 13 | Tosylate | 0.65 | 8.94 | 5.67 |
| EXAMPLE 14 | Palmitate | 0.66 | 6.89 | 3.67 |
| EXAMPLE 15 | Fumarate | 0.56 | 9.12 | 6.54 |
| EXAMPLE 16 | Tartrate | 0.63 | 6.89 | 3.33 |
| EXAMPLE 17 | Ascorbate | 0.56 | 18.98 | 6.66 |

The results show that the stability of the hydrochloride salt of the compound shown in Formula (I) is significantly higher than that of other salts.

Experimental Example 4 Pharmacokinetic Test

The compound shown in formula (I) and three kinds of salts having high solubility (i.e. the hydrochloride salt, mesylate and acetate prepared in Example 2, 10 and 12 respectively) were chosen to carry out the pharmacokinetic test. 48 male SD rats with a body weight of 200-220 g were randomly divided into 8 groups with 6 mice each group, administered the compound shown in Formula (I), the hydrochloride salt, mesylate and acetate thereof intragastrically (i.g.) and intravenously (i.v.) respectively, and the protocol was shown in Table 7:

TABLE 7

Experimental Protocol

| Group No. | Animal number | Compounds | Administration Mode | Dosage (mg/kg) | Administration Volume (ml/kg) |
|---|---|---|---|---|---|
| 1 | 6 | Compound shown in formula (I) | intragastrically | 40 | 10 |
| 2 | 6 | Hydrochloride salt | intragastrically | 40 | 10 |
| 3 | 6 | Acetate | intragastrically | 40 | 10 |
| 4 | 6 | Mesylate | intragastrically | 40 | 10 |
| 5 | 6 | Compound shown in formula (I) | intravenously | 20 | 10 |
| 6 | 6 | Hydrochloride salt | intravenously | 20 | 10 |
| 7 | 6 | Acetate | intravenously | 20 | 10 |
| 8 | 6 | Mesylate | intravenously | 20 | 10 |

Intragastric administration: 2% of HPMC
Intravenous administration: a solution prepared with 20% PEG The rats were fasted for 12 hours with free access to water prior to experiment; and fed together 2 hours after administration.

Blood sampling time points: 5 min (only administering intravenously), 0.25 h, 0.5 h, 1.0 h, 2.0 h, 4.0 h, 6.0 h, 8.0 h and 24 h after administration;

Sample treatment: 0.3 ml venous blood was obtained from rats' posterior ocular vein plexus at the above-mentioned time points, put into a heparinized tube, centrifuged for 5 minutes at 11000 rpm to separate plasma, then frozen in a refrigerator at −20° C.

Sample detecting and data analyzing:

The concentration of parent drugs in rat's plasma was detected by utilizing LC/MS/MS.

The pharmacokinetic parameters were calculated by the non-compartment method using WinNonlin 5.3 software (Pharsight, U.S.A.), the absolute bioavailability was calculated by the formula shown as below, the results were shown in Table 8:

$$F=(AUC_{i.g.} \times D_{i.v.})/(AUC_{i.v.} \times D_{i.g.}) \times 100\%$$

Wherein, F: absolute bioavailability; AUC: area under the curve; D: Dosage

TABLE 8

Results of Absolute Bioavailability

| Example | Name | Absolute Bioavailability (%) |
|---|---|---|
| EXAMPLE 1 | Compound shown in formula (I) | 2.2 |
| EXAMPLE 2 | Hydrochloride salt | 32.2 |
| EXAMPLE 10 | Mesylate | 7.32 |
| EXAMPLE 12 | Acetate | 5.34 |

The results show that the bioavailability of hydrochloride salt of the compound shown in Formula (I) is significantly higher than that of other salts.

Experimental Example 5 Assay of PIM Kinase Activity

Dose-dependent experiments on PIM1, PIM2 and PIM3 were commissioned to Shanghai Runnuo Biotechnology, 6 concentration gradients were set, the initial concentration was 30 nM, 200 nM and 30 nM, then diluted successively, the inhibitive effects of compounds on PIM kinase was tested, the results were shown in Table 9.

TABLE 9

Results of Effects to PIM Kinase

| Compound | IC50(nM) | | |
|---|---|---|---|
| | PIM 1 | PIM 2 | PIM 3 |
| Compound shown in formula (I) (Prepared in EXAMPLE 1) | 10.01 | 8.09 | 22.98 |
| Hydrochloride salt of Compound shown in formula (I) (Prepared in EXAMPLE 2) | 2.31 | 1.54 | 4.36 |

The results show that the hydrochloride salt of the compound shown in Formula (I) exhibits very strong inhibitive effect on PIM kinase.

In the end, the applicant believes that those skilled in the art are capable of replacing chloride acid with other inorganic acid or organic acid and utilizing the method of the present invention or those similar to the present invention to prepare different acid addition salts of the compound shown in Formula (I), or obtaining the amorphous solid, solvate or other crystals of hydrochloride salt of the compound shown in Formula (I) of the present invention by using chloride acid on the basis of the present invention, however, compared with other acid addition salts, the amorphous solid, solvate or other crystals, the hydrochloride salt of the compound shown in Formula (I) has significant technical advantages.

The invention claimed is:

1. A hydrochloride salt of a compound shown in Formula (I), wherein the structure of the hydrochloride salt is shown in Formula (II):

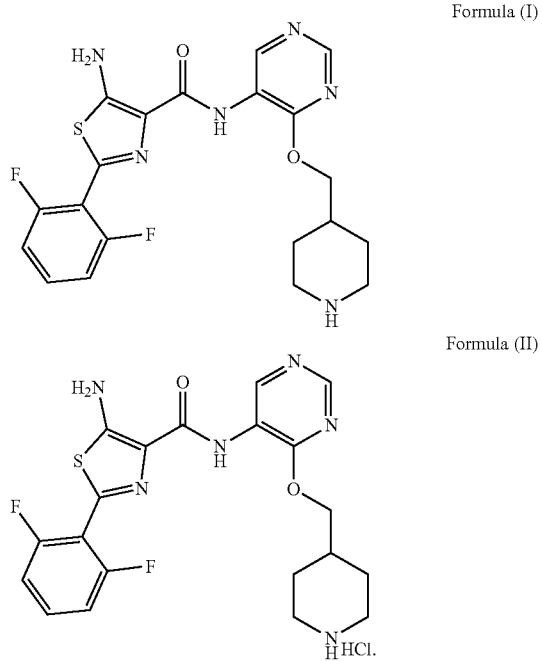

2. The hydrochloride salt according to claim 1, wherein the hydrochloride salt is present in a crystalline form.

3. The hydrochloride salt according to claim 2, wherein the X-ray powder diffraction pattern of the crystalline form of the hydrochloride salt includes the diffraction peaks at 2θ of 6.8±0.2°, 9.5±0.2°, 11.4±0.2°, 15.0±0.2°, 17.0±0.2°, 19.9±0.2°, 20.3±0.2°, 20.6±0.2°, 22.9±0.2°, 23.6±0.2°, 24.9±0.2°, 26.1±0.2° and 26.6±0.2°.

4. A method for preparing the hydrochloride salt according to claim 1 comprising dissolving the compound shown in Formula (I) in a solvent, controlling the reaction temperature, adding a methanol solution of hydrogen chloride, reacting for 0~24h under maintaining the reaction temperature, precipitating a solid from the reaction solution, filtering and drying under vacuum.

5. The method according to claim 4, wherein the reaction temperature is controlled at 0~30° C.;
after adding the methanol solution of hydrogen chloride, the reaction lasts for 30 minutes to 24 hours, under maintaining the reaction temperature; and
the temperature of the drying under vacuum is 50° C.

6. The method according to claim 4, wherein the method comprises dissolving the compound shown in Formula (I) in the solvent, heating it to 50~200° C., adding the methanol solution of hydrogen chloride, reacting for 0~24 hours at temperature of 50 to 100° C., then cooling down to 20~30° C., precipitating the solid from the reaction solution, filtering and drying under vacuum.

7. The method according to claim 6, wherein the compound shown in Formula (I) is dissolved in the solvent and then heated to 50~60° C.;
after adding the methanol solution of hydrogen chloride, the reaction lasts for 0~24 hours; and
the temperature of the drying under vacuum is 50° C.

8. The method according to claim 4, wherein the solvent is one or more selected from the group consisting of methanol, dichloromethane, dimethyl sulfoxide, tetrahydrofuran, dimethylformamide, acetone, ethanol, acetonitrile, propanol, butanol, N-methylpyrrolidone, ethyl acetate and water;
the concentration of the methanol solution of hydrogen chloride is 0.25 mol/L~2 mol/L; and
the mole ratio of the methanol solution of hydrogen chloride to the compound shown in Formula (I) is 0.1~10: 1.

9. A pharmaceutical composition, wherein the pharmaceutical composition comprises the hydrochloride salt according to claim 1 as an active component;
the pharmaceutical composition further comprises a pharmaceutically acceptable carrier or excipient; and
the pharmaceutical composition is in the form of tablet, capsule, pill, granule, powder, suppository, injection, solution, suspension, ointment, patch, lotion, drops, liniment or spray.

10. A method for treating diseases caused by overexpression of PIM kinase comprising administering an effective dose of the hydrochloride salt of the compound shown in Formula (I) according to claim 1 to a subject in need thereof; and
the subject is a mammal.

11. A method for treating diseases caused by overexpression of PIM kinase comprising administering an effective dose of the hydrochloride salt of the compound shown in Formula (I) according to claim 1 to a subject in need thereof, wherein the diseases include tumor, autoimmune diseases, allergic diseases, atherosclerosis disease and rejection resulting from organ transplants, and the subject is a mammal.

12. The hydrochloride salt according to claim 2, wherein the X-ray powder diffraction pattern of the crystalline form of the hydrochloride salt further includes the diffraction peaks at 2θ of 12.0±0.2°, 28.8±0.2°, 29.1±0.2°, 32.5±0.2° and 34.7±0.2°.

13. The method according to claim 4, wherein the reaction temperature is controlled at 0° C. or 20~30° C.;
   after adding the methanol solution of hydrogen chloride, the reaction lasts for 30 minutes under maintaining the reaction temperature; and
   the temperature of the drying under vacuum is 50° C.

14. The method according to claim 4, wherein the method comprises dissolving the compound shown in Formula (I) in the solvent, heating it to 50~100° C., adding the methanol solution of hydrogen chloride, reacting for 0~24 hours at temperature of 50 to 100° C., then cooling down to 20~30° C., precipitating the solid from the reaction solution, and filtering and drying under vacuum.

15. The method according to claim 6, wherein the compound shown in Formula (I) is dissolved in the solvent and then heated to 50~60° C.;
   after adding the methanol solution of hydrogen chloride, the reaction lasts for 5~10 hours at temperature of 50~60° C.; and
   the temperature of the drying under vacuum is 50° C.

16. The method according to claim 4, wherein the solvent is one or more selected from the group consisting of methanol, dichloromethane, dimethyl sulfoxide, tetrahydrofuran, dimethylformamide, acetone, ethanol, acetonitrile, N-methylpyrrolidone, ethyl acetate and water.

17. The method according to claim 4, wherein the solvent is methanol and dichloromethane, dimethyl sulfoxide and tetrahydrofuran, dimethylformamide and acetone, ethanol and acetonitrile, N-methylpyrrolidone and ethyl acetate, N-methylpyrrolidone and water, or N-methylpyrrolidone.

18. The method according to claim 4, wherein the solvent is dimethylformamide and acetone.

19. The method according to claim 4, wherein a concentration of the methanol solution of hydrogen chloride is 0.5 mol/L~1 mol/L.

20. The method according to claim 4, wherein a mole ratio of the methanol solution of hydrogen chloride to the compound shown in Formula (I) is 1~1.5: 1.

* * * * *